United States Patent
Ramy

(10) Patent No.: US 8,580,328 B2
(45) Date of Patent: Nov. 12, 2013

(54) SALT SUBSTITUTE AND COMPOSITION, FOR EXAMPLE FOOD COMPOSITION, COMPRISING IT

(76) Inventor: Hubert Ramy, Saint-Denis de la Réunion (FR)

( * ) Notice: Subject to any disclaimer, the term of this patent is extended or adjusted under 35 U.S.C. 154(b) by 354 days.

(21) Appl. No.: 12/515,081

(22) PCT Filed: Nov. 15, 2007
(Under 37 CFR 1.47)

(86) PCT No.: PCT/FR2007/001881
§ 371 (c)(1),
(2), (4) Date: Mar. 30, 2010

(87) PCT Pub. No.: WO2008/068419
PCT Pub. Date: Jun. 12, 2008

(65) Prior Publication Data
US 2011/0097475 A1   Apr. 28, 2011

(30) Foreign Application Priority Data
Nov. 17, 2006   (FR) ...................... 06 10108

(51) Int. Cl.
*A23L 1/22*   (2006.01)

(52) U.S. Cl.
USPC ............. 426/549; 426/74; 426/615; 426/626; 426/648

(58) Field of Classification Search
USPC ............................ 426/74, 549, 615, 626, 648
See application file for complete search history.

(56) References Cited

U.S. PATENT DOCUMENTS

| | | | |
|---|---|---|---|
| 3,934,045 A | 1/1976 | Fernholz et al. | |
| 4,165,386 A | 8/1979 | Kikuhara | |
| 5,260,091 A | 11/1993 | Locke et al. | |
| 6,013,298 A | 1/2000 | Takano et al. | |

FOREIGN PATENT DOCUMENTS

| | | | |
|---|---|---|---|
| EP | 0667107 | | 8/1995 |
| FR | 19820001118 | * | 1/1982 |
| JP | 52-156951 | | 12/1977 |
| JP | 54-20156 | | 2/1979 |
| JP | 56-140878 | | 11/1981 |
| JP | 57-105176 | | 6/1982 |
| JP | 61-219336 | | 9/1986 |
| JP | 404179436 | * | 6/1992 |
| JP | 04-59860 | | 9/1992 |
| JP | 07-008239 | | 1/1995 |
| JP | 09-238643 | | 9/1997 |
| JP | 10-014481 | | 1/1998 |
| JP | 11-075671 | | 3/1999 |
| JP | 2001-333752 | | 12/2001 |
| JP | 2004-283087 | | 10/2004 |
| JP | 2007020537 | * | 2/2007 |
| WO | WO 97/40705 | | 11/1997 |
| WO | WO 98/07324 | | 2/1998 |

OTHER PUBLICATIONS

Baldini et al. "Reduction of the quantity of NaCl used in dried meat products"; Viande et produits carnés, 1984, vol. 5(3), 83-88. (+ English abstract).
Hellemann U, "Perceived taste of NaCl and acid mixtures in water and bread", Int. J. of Food Sci. & techn., 1992, vol. 27(2) 201-211.
Lahtinen S, "Masking of the bitter taste of salt substitutes with lactose in food emulsions", J. of Food quality, 1986, vol. 9(4), 199-204.
Gildberg et al;, "Acceleration of autolysis during fish sauce fermentation by adding acid and reducing the salt content", J. of the Sc. of Food and Agriculture, 1984, vol. 35(12), 1363-1369.

* cited by examiner

*Primary Examiner* — Helen F Heggestad
(74) *Attorney, Agent, or Firm* — Harness, Dickey & Pierce, P.L.C.

(57) ABSTRACT

Methods for replacing salt in a food composition comprising substituting all or part of the salt in the food composition with vinegar, while conserving the food composition's gustative, olfactive and physical values the presence of salt instead of the vinegar would give. In various embodiments, the food composition is a product of bakery comprising water, salt, yeast, and flour or a mix of flours. For example, vinegar may replace at least 60% of the salt in the food composition, and may have an acidity of 3% to 10%.

14 Claims, No Drawings

SALT SUBSTITUTE AND COMPOSITION, FOR EXAMPLE FOOD COMPOSITION, COMPRISING IT

CROSS-REFERENCE TO RELATED APPLICATIONS

This application is a National Phase Entry of International Application No. PCT/FR2007/001881, filed Nov. 15, 2007, which claims priority to French Patent Application No. 06/10108, filed Nov. 17, 2006, both of which are incorporated herein by reference.

BACKGROUND AND SUMMARY

The present invention relates to a salt substitute, that is a substance able to replace totally or partially the salt in a recipe by playing the same role, that is to be able to give to the product that is made with this substitute, the salty taste and the other qualitative and taste attributes the presence of salt would give. Thereby, the invention relates to pharmacological, cosmetics, food, functional food, nutraceuticals and veterinary compositions field, where a salty taste is wanted but where the salt would be absent or in very low quantity compared to what is generally used.

Excess of salt consumption in all its forms is a public health problem. Every year, 12 000 000 people in the world and 25 000 people in France die because of salt overdose. Indeed, an overly important salt consumption thickens the blood, gradually blocks the arteries, causes hypertension, possibly causes myocardial infarction, a blood clot in the brain and a cerebrovascular accident, osteoporosis, hypertension, cancers, etc. In terms of hypertension, salt has been considered for years as a major danger. Hypertension affects about 7 millions french people and is a strong risk factor for cardiovascular disease, the number one cause of mortality in France. Furthermore, it seems salt excess is correlated with left ventricular hypertrophy, an important risk factor for cardiovacular disease appearance.

Regarding osteoporosis field, it is known that bone is constructed with available calcium, however all the intaken calcium is not assimilated. Part of the calcium is evacuated in urine and salt increases this excretion. The more the diet is salty, the more the calcium leaks are important. Finally, salt is also involved in cancer incidence, in particular in gastric carcinoma incidence. Therefore, it is recommended not to make excesses of salt or of products conserved by salting, delicatessen (<<charcuteries>> in french).

Salt excess is therefore very strongly suspected of being involved in the appearance and aggravation of numerous serious diseases. Yet salt is widely used in food-industry because it is cheap and it also increases taste, masks bitter flavours and gives food relief. Consequently, transformed products contain excessive quantities of salt compared to the amount the body needs, which according to WHO is about 5 grams per day. For example, a sandwich with delicatessen and cheese contains in average 4 g of salt. Besides, there is a lot of salt in bread (a french stick contains about 4 g), delicatessen, cheese, pastries, cereals, cooked dishes, prepared soups, pastas, appetizer biscuits and cakes, peanuts, anchovies, hamburgers, pizzas, etc.

French people consume about 7.9 g of salt, and even more, so much so it is difficult to measure exactly the quantity of salt everyone adds into his food. 10% of them consume more than 12 g per day, and some consume 25 g per 24 hours. Consequently there is an urgent need to have a substance able to replace salt totally or partially so as to limit the quantity of salt in these compositions while preserving their salty taste.

This goal is reached according to the invention thanks to the use of vinegar or an equivalent of it as a substitute for all or part of the salt used for the making of a composition. It can concern food, pharmaceutical, cosmetic, functional food, nutraceutical and veterinary compositions or an intermediate composition which is part of the constitution of these compositions. The invention relates of course to any kind of vinegar and notably to wine or cidre vinegar, and more generally to fruit, cereal, malt, rice, corn, milk, etc. vinegars. Therefore, we can mention a vinegar with an acidity dosed approximately between 3 to 10%, more preferably 5% acidity.

We hereby understand by vinegar equivalent, a product with a strong acidity, except acetic acid concentrated at more than about 50%, particularly at more than about 85%. Vinegar is an aqueous solution with a strong acidity, resulting from wine or another alcoholized liquid fermentation. Thus, it contains particles and substances coming from the plant which gives it its different properties.

Vinegar or one of its equivalents according to the invention can be presented in a liquid or a solid form, for example in a dried powder form when for instance it concerns a dehydrated product, or even a freeze-dried product. Therefore it can be a free dehydrated form or a dehydrated form associated to a support, particularly food support like flour or another product such as maltodextrine for instance. But it can also concern other supports like cosmetic or pharmaceutical supports for example, depending on the composition's field of application. As an example, in a composition based on flour, vinegar or an equivalent of vinegar in a liquid form can be used to replace all or part of the salt at the rate of 0.2% to 5% of flour weight, that is in the order of 2 to 50 g per flour kg. In the case of vinegar or an equivalent of it in dehydrated form, it can be used at the rate of 1 liter for about 95 g of flour, that is in the order of 0.05 to 5% of flour weight, that is again in the order of 0.5 to 50 g per flour kilo.

The use of vinegar or one of its equivalents according to the present invention is remarkable because it enables to decrease the quantity of salt generally contained in food by at least 60% while conserving their properties and notably their gustative value. The invention is remarkable because vinegar or an equivalent of it also allows at least a 33% yeast quantity decrease in all the bakery products and up to the order of a 40% sugar decrease or even more in all sweetened products. The use of vinegar or an equivalent of it instead of salt also allows on a nutritional point of view to approximately a 30% decrease of the induced glycemia increase compared to normal bread, and we can observe a lower and slower absorption (about 30%) of the sugars found in the bakery products.

Vinegar or one of its equivalents can be used according to the invention as a replacement of all or a part of the salt in the composition without making substantial modifications in the preparation process. The person skilled in the art can determine variants for these processes of preparation likely to enable the replacement of salt by vinegar without modifying the aspect or the other gustative properties of the compositions. Indeed, thanks to the invention, we can replace an important part of the salt contained notably in food, more particularly in bakery products like bread, viennese pastry, puff pastry, shortcrust pastry and shortbread dough, biscuits, sourdoughs. But the invention can also apply to pastry, delicatessen, cheese industry, cereals, cooked dishes, prepared soups, pastas, apetizer cakes, hamburgers, pizzas, etc.

Of course, this invention also relates to a composition such as defined hereabove comprising vinegar or an equivalent of it instead of all or part of the salt normally present. It can concern notably food, pharmaceutical, cosmetic, functional food, nutraceutical or veterinary compositions, or an intermediary composition which is part of the constitution of these compositions, characterized by the fact that it contains vinegar or it has been made with vinegar as a substitute of all or part of the salt generally present in the said composition. An example of such a composition can be for instance flour associated with dehydrated vinegar.

The invention also relates to the making process of these compositions which consists in blending the vinegar or a vinegar equivalent instead of all or part of the salt normally present. The use of vinegar according to this invention allows to suppress alkalinizing food such as sugars which are abundantly used in bakery, pastry, biscuits, meats, fish, fruits and vegetables. Another advantage of the invention resides in the fact that the presence of vinegar or an equivalent in the flour storerooms, in artisans' millers' as well as industrials' storehouses, spares the use of insecticides, to decimate all insects such as Curculionidae, mites, sawtoothed grain beetles, etc. Besides, the use of vinegar according to the invention enables to decrease and even to suppress salt in brines used notably in delicatessen and meat conservation.

Additional advantages and characteristics of the invention will appear from the following examples concerning the use of vinegar as a substitute of all or part of the salt in the preparation of bakery products. In the following examples the used vinegar is cidre vinegar which is called in the examples <<"R" product>>, but any other vinegar or equivalent of it except the ones that have a very strong acidity as mentioned previously, can be used.

DETAILED DESCRIPTION

Bread is the most representative among bakery products. Traditional bread contains in the order of 20 g salt per flour kilo, and brings important risks for health. The examples hereafter show the use of the "R" product according to the invention enables to replace the major part of salt, and to have a 33% yeast decrease and a 40% sugar decrease and therefore prevents health risks.

Example 1

Traditional Bread Manufacturing

For this battery of tests the "R" product has been used in a liquid originating from organic culture "BIO" with 5% acidity dosage.

I—Traditional Bread Recipe
1) The baker's control recipe:

| | |
|---|---|
| Type 65 Flour | 1 kg |
| Yeast | 30 g |
| Water | 620 g |
| Salt | 20 g |
| "R" product | 0 g |
| Improver(Stabilizer) | 4 g |
| Dough mixing | |
| 1st speed | 3 mn |
| 2nd speed | 6 mn |
| Dividing, shaping | |
| Dough proofing ("pointage" in french) | 80 mn |
| Temperature | 22° C. |
| Baking in a deck oven | 20 mn to 240° C. |

2) Recipe with liquid "R" product (test 1):

| | |
|---|---|
| Type 65 Flour | 1 kg |
| Yeast | 20 g |
| Water | 620 g |
| Salt | 8 g |
| Liquid "R" product | 8 g |
| Improver(Stabilizer) | 4 g |
| Dough mixing | |
| 1st speed | 3 mn |
| 2nd speed | 6 mn |
| Dividing, shaping | |
| Dough proofing | 80 mn |
| Temperature | 22° C. |
| Baking in deck oven | 20 mn to 240° C. |

3) Recipe with liquid "R" product (test 2):

| | |
|---|---|
| Type 65 Flour | 1 kg |
| Yeast | 20 g |
| Water | 620 g |
| Salt | 8 g |
| Liquid "R" product | 16 g |
| Improver(Stabilizer) | 8 g |
| Dough mixing | |
| 1st speed | 3 mn |
| 2nd speed | 6 mn |
| Dividing, shaping | |
| Dough proofing | 80 mn |
| Temperature | 22° C. |
| Baking in a deck oven | 20 mn to 240° C. |

II—Traditional Bread Recipe Prepared the Day Before for a Baking the Day After
1) The baker's control recipe:

| | |
|---|---|
| Type 65 Flour | 1 kg |
| Yeast | 30 g |
| Water | 620 g |
| Salt | 20 g |
| "R" product | 0 g |
| Improver(Stabilizer) | 4 g |
| Dough mixing | |
| 1st speed | 3 mn |
| 2nd speed | 6 mn |
| Dividing, Shaping | |
| Fermentation | 18 h in room |
| Temperature | 22° C. |
| baking in a deck oven | 20 mn to 240° C. |

2) Recipe with liquid "R" product (test 1):

| | |
|---|---|
| Type 65 flour | 1 kg |
| Yeast | 20 g |
| Water | 620 g |
| Salt | 8 g |
| "R" product | 12 g |
| Improver(Stabilizer) | 4 g |
| Dough mixing | |
| 1st speed | 3 mn |
| 2nd speed | 6 mn |
| Dividing, Shaping | |
| Fermentation | 18 h in room |
| Temperatur | 22° C. |
| Baking in a deck oven | 20 mn to 240° C. |

III—Conclusions

During the manufacturing process, the addition of the "R" product to the different proportionings tested has revealed no nuisance in the mixing process (whatever the different ingredients' mixing order was) during the dough mixing, dough proofing and baking processes.

Olfactory Aspect:

There is no odor difference between the control and the different recipes comprising the "R" product, the perfumes are identical in savour and intensity.

Physical Aspect:

The recipes tested with the 3 dosages of the "R" product have enabled to obtain products with perfect texture and alveoling ("alveolage" in french), identical to the control. The color of the crust and of the crumb shows no difference compared to the recipe usually used by the baker.

Gustative Aspect:

No significant difference in taste has been noticed when the 3 tests and the control have been tasted. The addition of the "R" product in the recipe thus allows a 33% yeast decrease as well as the suppression of 60% of salt.

Example 2

Viennese Pastry Manufacturing (Pain Au Chocolat (Chocolate-Filled Roll), Croissant, Circular Pastry Made with Sweetened Dough and Raisins, Apple Turnover, French Stick, Puff Pastry, Meat Pie, Maccatias, Etc.)

For this battery of tests the "R" product has been used in a liquid form originating from organic culture "BIO" with 5% acidity dosage.

1) The baker's control recipe with 20 hours freezing:

| Type 65 flour | 1 kg |
| Yeast | 30 g |
| Caster sugar | 120 g |
| Water | 500 g |
| Butter | 500 g |
| Salt | 20 g |
| "R" product | 0 g |
| Dough mixing | |
| | |
| 1st speed | 3 mn |
| 2nd speed | 5 mn |
| Fermentation Fridge | 18 h |
| Temperature | 4° C. |
| Dividing, Shaping | |
| Freezing | 20 h |
| Temperature | minus 20° C. |
| Baking in a Ventilated Oven | 18 mn to 175° C. |

2) Recipe with the "R" product and 20 hours freezing:

| Type 65 Flour | 1 kg |
| Yeast | 25 g |
| Caster sugar | 72 g |
| Water | 500 g |
| Butter | 500 g |
| Salt | 8 g |
| "R" product | 12 g |
| Dough mixing | |
| | |
| 1st speed | 3 mn |
| 2nd speed | 5 mn |
| Fermentation Fridge | 18 h |
| Temperature | 4° C. |
| Dividing, Shaping | |
| Freezing | 20 h |
| Temperature | minus 20° C. |
| Baking in a Ventilated Oven | 18 mn to 175° C. |

3) The baker's control recipe with 120 hours freezing:

| Type 65 Flour | 1 kg |
| Yeast | 30 g |
| Caster sugar | 120 g |
| Water | 500 g |
| Butter | 500 g |
| Salt | 20 g |
| "R" product | 0 g |
| Dough mixing | |
| | |
| 1st speed | 3 mn |
| 2nd speed | 5 mn |
| Fermentation Fridge | 18 h |
| Temperature | 4° C. |
| Dividing, Shaping | |
| Freezing | 120 h |
| Temperature | minus 20° C. |
| Baking in a Ventilated Oven | 18 mn to 175° C. |

4) Recipe with the "R" product and 120 hours freezing:

| Type 65 Flour | 1 kg |
| Yeast | 25 g |
| Caster sugar | 72 g |
| Water | 500 g |
| Butter | 500 g |
| Salt | 8 g |
| "R" product | 12 g |
| Dough mixing | |
| | |
| 1st speed | 3 mn |
| 2nd speed | 5 mn |
| Fermentation Fridge | 18 h |
| Temperature | 4° C. |
| Dividing, Shaping | |
| Freezing | 120 h |
| Temperature | minus 20° C. |
| Baking in a Ventilated Oven | 18 mn to 175° C. |

5) Conclusions:

During the manufacturing process, the addition of "R" product to the different proportionings tested has revealed no nuisance in the mixing process (whatever the different ingredients' mixing order was) during the dough mixing, dough proofing and baking processes.

Olfactory Aspect:

There is no odor difference between the control and the different recipes comprising the "R" product, the perfumes are identical in savour and intensity.

Physical Aspect:

Pastries obtained from the 2 tests and the control recipe show no difference in color or texture.

Gustative Aspect:

Croissants and chocolate-filled rolls from the 2 tests as well as the ones from the control recipe show no difference in taste. The addition of the "R" product in the recipe thus allows a 15% yeast decrease, the suppression of 60% of salt, as well as a 40% sugar decrease. Same tests have been performed fresh without freezing, the results are identical.

Example 3

Utilization of "R" Product having 5% Acidity Dosage, Dehydrated and Fixed on Flour (1 Liter "R" Product Fixed on 95 g Flour for Alimentary Use)

For this battery of tests, "R" product has been used in a liquid form originating from organic culture BIO 5% acidity dosed and dehydrated on 95 g of flour for alimentary use.

1) The baker's traditional recipe (control Test):

| | |
|---|---|
| Type 65 Flour | 1 kg |
| Yeast | 30 g |
| Water | 620 g |
| Salt | 20 g |
| Dehydrated "R" product | 0 g |
| Improver (Stabilizer) | 4 g |
| Dough mixing: | |
| 1st speed | 3 mn |
| 2nd speed | 5 mn |
| Dough proofing | 15 mn |
| Temperature | 22° C. |
| Dividing, Shaping | |
| Fermentation in room | 45 mn |
| Temperature | 22° C. |
| Baking in a deck oven | 25 mn to 240° C. |

2) Recipe with the liquid "R" product (control):

| | |
|---|---|
| Type 65 Flour | 1 kg |
| Yeast | 30 g |
| Water | 620 g |
| Salt | 8 g |
| Liquid "R" product | 12 g |
| Improver (Stabilizer) | 4 g |
| Dough mixing: | |
| 1st speed | 3 mn |
| 2nd speed | 5 mn |
| Dough proofing | 15 mn |
| Temperature | 22° C. |
| Dividing, Shaping | |
| Fermentation in room | 45 mn |
| Temperature | 22° C. |
| Baking in a deck oven | 25 mn to 240° C. |

3) Recipe with the "R" product (test 1):

| | |
|---|---|
| Type 65 Flour | 1 kg |
| Yeast | 20 g |
| Water | 620 g |
| Salt | 8 g |
| Dehydrated "R" product and fixed on flour | 2 g |
| Improver (Stabilizer) | 4 g |
| Dough mixing: | |
| 1st speed | 3 mn |
| 2nd speed | 5 mn |
| Dough proofing | 15 mn |
| Temperature | 22° C. |
| Dividing, Shaping | |
| Fermentation in room | 45 mn |
| Temperature | 22° C. |
| Baking in a deck oven | 25 mn to 240° C. |

3) Recipe with the "R" product (test 2):

| | |
|---|---|
| Type 65 Flour | 1 kg |
| Yeast | 20 g |
| Water | 620 g |
| Salt | 8 g |
| "R" product dehydrated and fixed on flour | 4 g |
| Improver (Stabilizer) | 4 g |
| Dough mixing: | |
| 1st speed | 3 mn |
| 2nd speed | 5 mn |
| Dough proofing | 15 mn |
| Temperature | 22° C. |
| Dividing, Shaping | |
| Fermentation in room | 45 mn |
| Temperature | 22° C. |
| Baking in a deck oven | 25 mn to 240° C. |

4) Recipe with the "R" product (test 3):

| | |
|---|---|
| Type 65 Flour | 1 kg |
| Yeast | 20 g |
| Water | 620 g |
| Salt | 8 g |
| Dehydrated "R" product and fixed on flour | 6 g |
| Improver (Stabilizer) | 4 g |
| Dough mixing: | |
| 1st speed | 3 mn |
| 2nd speed | 5 mn |
| Dough proofing | 15 mn |
| Temperature | 22° C. |
| Dividing, Shaping | |
| Fermentation in room | 45 mn |
| Temperature | 22° C. |
| Baking in a deck oven | 25 mn to 240° C. |

5) Recipe with the "R" product (test 4):

| | |
|---|---|
| Type 65 Flour | 1 kg |
| Yeast | 20 g |
| Water | 620 g |
| Salt | 0 g |
| "R" product dehydrated and fixed on flour | 4 g |
| Improver (Stabilizer) | 4 g |
| Dough mixing: | |
| 1st speed | 3 mn |
| 2nd speed | 5 mn |
| Dough proofing | 15 mn |
| Temperature | 22° C. |
| Dividing, Shaping | |
| Fermentation in room | 45 mn |
| Temperature | 22° C. |
| Baking in a deck oven | 25 mn to 240° C. |

6) Conclusions:

During the manufacturing process, the addition of "R" product to the different proportionings tested has revealed no nuisance in the mixing process (whatever the different ingredients' mixing order was) during the dough mixing, dough proofing and baking processes.

Olfactory Aspect:

There is no odor difference between the control and the different recipes "R" Santé, the perfumes are identical in savour and intensity.

Physical Aspect:

The recipes tested in tests 1, 2 and 3 have enabled to obtain products with perfect texture and alveoling, identical to the control. The color of the crust and the crumb shows no difference compared to the recipe usually used by the baker.

Gustative Aspect:

No significant difference in taste has been noticed when the 5 tests and the control have been tasted. However, the best balance is reached for a 4 g dehydrated "R" product dosage (test 2) and in test 5 salt has been totally suppressed. Whether it's in liquid or dehydrated form, the addition of "R" product to the different recipes keeps the same advantages, namely at least a 60% salt decrease and a 33% yeast decrease.

Other tests have been performed with different concentrations (1 liter "R" product fixed on 450 g flour and 1 liter on 750 g flour), with acidity rates between 4 and 10%. These test yielded identical results proportionals to the quantities and percentages.

Example 4

Tests with Acetic Acid 85% Concentrated

1) Baker's recipe with "R" product:

| | |
|---|---|
| Type 65 Flour | 1 kg |
| Yeast | 30 g |
| Water | 620 g |
| Salt | 20 g |
| "R" product | 0 g |
| Improver(Stabilizer) | 4 g |
| Dough mixing: | |
| 1st speed | 3 mn |
| 2nd speed | 6 mn |
| Dividing, Shaping | |
| Dough proofing | 45 mn |
| Temperature | 22° C. |
| Fermentation in room | 15 mn |
| Temperature | 22° C. |
| Baking in a deck oven | 20 mn to 240° C. |

2) Test 1 with acetic acid:

| | |
|---|---|
| Type 65 Flour | 1 kg |
| Yeast | 20 g |
| Water | 620 g |
| Salt | 8 g |
| Acetic Acid 85% | 2 g |
| Improver(Stabilizer) | 4 g |
| Dough mixing: | |
| 1st speed | 3 mn |
| 2nd speed | 6 mn |
| Dividing, Shaping | |
| Dough proofing | 45 mn |
| Temperature | 22° C. |
| Fermentation in room | 15 mn |
| Temperature | 22° C. |
| Baking in a deck oven | 20 mn to 240° C. |

3) Test 2 with acetic acid:

| | |
|---|---|
| Type 65 Flour | 1 kg |
| Yeast | 20 g |
| Water | 620 g |
| Salt | 8 g |
| Acetic Acid 85% | 4 g |
| Improver(Stabilizer) | 4 g |
| Dough mixing: | |
| 1st speed | 3 mn |
| 2nd speed | 6 mn |
| Dividing, Shaping | |
| Dough proofing | 80 mn |
| Temperature | 22° C. |
| Fermentation in room | 15 mn |
| Temperature | 22° C. |
| Baking in a deck oven | 20 mn to 240° C. |

4) Test 3 with acetic acid:

| | |
|---|---|
| Type 65 Flour | 1 kg |
| Yeast | 20 g |
| Water | 620 g |
| Salt | 8 g |
| Acetic Acid 85% | 8 g |
| Improver(Stabilizer) | 4 g |
| Dough mixing: | |
| 1st speed | 3 mn |
| 2nd speed | 6 mn |
| Dividing, Shaping | |
| Dough proofing | 80 mn |
| Temperature | 22° C. |
| Fermentation in room | 15 mn |
| Temperature | 22° C. |
| Baking in a deck oven | 20 mn to 240° C. |

5) Test 4 with acetic acid:

| | |
|---|---|
| Type 65 Flour | 1 kg |
| Yeast | 20 g |
| Water | 620 g |
| Salt | 8 g |
| Acetic Acid 85% | 13 g |
| Improver(Stabilizer) | 4 g |
| Dough mixing: | |
| 1st speed | 3 mn |
| 2nd speed | 6 mn |
| Dividing, Shaping | |
| Dough proofing | 80 mn |
| Temperature | 22° C. |
| Fermentation in room | 15 mn |
| Temperature | 22° C. |
| Baking in a deck oven | 20 mn to 240° C. |

6) Conclusions:

During the manufacturing process the addition of 85% concentrated acetic acid above 2 g provokes 70% yeast destruction and does not allow a correct rise of the dough.

Olfactory Aspect:

Acetic acid, in a 2 g dosage, does not generate odor differences compared to the control. Above 4 g acetic acid, a strong smell is emitted during manipulations as well as during the baking which can cause irritation problems.

Physical Aspect:

For test 1, that is 2 g acetic acid, we observe no significant texture and alveoling differences. For all the other dosages, as acetic acid provoked the destruction of yeasts, The dough rise has been totally canceled and so a bread unfitted for consumption is produced.

Gustative Aspect:

For test 1, that is 2 g acetic acid, The taste of bread is blander than the control. For all the other tests, the increase of the acetic acid dose yields a bitter taste with an intensity that increases proportionally to the dose of acid.

Therefore we can consider the substitution of "R" product by acetic acid does not enable to keep the physical, olfactory and gustative qualities of the control recipe and produces a bread unfitted for consumption.

The invention claimed is:

1. A process for replacing salt in a food composition comprising substituting at least 60% of the salt in the food composition with vinegar having an acidity of 3% to 10%, while conserving the food composition's gustative, olfactive and physical values the presence of salt instead of the vinegar would give, said food composition being a product of bakery comprising, prior to the substituting, water, salt, and yeast, and flour or a mix of flours.

2. The process according to claim 1, wherein the product of bakery is a bread or Viennese pastry.

3. The process according to claim 1, wherein the vinegar is selected from the group consisting of wine vinegar, cider vinegar, fruit vinegar, cereal vinegar, malt vinegar, rice vinegar, corn vinegar, and milk vinegar.

4. The process according to claim 1, wherein the vinegar is in a liquid or a solid form.

5. The process according to claim 1, wherein the vinegar is in a free dehydrated form or a dehydrated form associated to the food composition.

6. The process according to claim 1, wherein in a composition based on flour, vinegar in a liquid form is used to replace all or part of the salt at the rate of 0.2% to 5% of flour weight, that is in an order of 2 to 50 g per flour kg and in the case of vinegar in dehydrated form, it is used at the rate of 1 liter for about 95 g of flour, that is in the order of 0.05 to 5% of flour weight, that is again in the order of 0.5 to 50 g per flour kilo.

7. A food composition chosen from the group consisting of a product of bakery, pastry, cheese, cereals, cooked dishes, prepared soups, pastas, appetizer cakes, hamburgers and pizzas, comprising vinegar having an acidity of 3% to 10% as a substitute for at least 60% of the salt generally present in it.

8. The composition according to claim 7, wherein the composition comprises flour associated in the composition with dehydrated vinegar or an equivalent of it.

9. A method for making a baked good comprising baking a composition comprising: flour, yeast, water, and vinegar having an acetic acid concentration of 2% to 10%, wherein the baked good has gustative, olfactive and physical values equivalent to a reference composition comprising flour, yeast, water, and salt, wherein at least 60% of the salt in the reference composition is replaced with vinegar in the baked good.

10. The method according to claim 9, wherein the baked good has a liquid vinegar concentration of 0.2% to 5% (w/w) relative to the flour.

11. The method according to claim 9, wherein the baked good has a dehydrated vinegar concentration of 0.05% to 5% (w/w) relative to the flour.

12. The method according to claim 9, wherein the vinegar is selected from the group consisting of wine vinegar, cider vinegar, fruit vinegar, cereal vinegar, malt vinegar, rice vinegar, corn vinegar, and milk vinegar.

13. A method for making a baked good comprising baking a composition comprising:
   (a) flour;
   (b) yeast;
   (c) an acid consisting of vinegar having an acetic acid concentration of 2% to 10%, at a level of from 0.05% to 5%, by weight of the flour; and
   (d) water;
   wherein the baked good has gustative, olfactive and physical values equivalent to a reference composition comprising flour, yeast, water, and salt, and
   wherein at least 60% of the salt in the reference composition is replaced with the acid in the baked good.

14. The method according to claim 13, wherein the vinegar is selected from the group consisting of wine vinegar, cider vinegar, fruit vinegar, cereal vinegar, malt vinegar, rice vinegar, corn vinegar, and milk vinegar.

* * * * *